(12) United States Patent
Baber et al.

(10) Patent No.: US 10,799,172 B2
(45) Date of Patent: Oct. 13, 2020

(54) MULTIFUNCTIONAL MEASURING DEVICE FOR AUTOMATIC EXAMINATION OF FEMALE GENITAL ORGANS

(71) Applicant: LADYSENSE (2017) LTD., Ramat Gan (IL)

(72) Inventors: Alex Baber, Ramat Gan (IL); Boris Zhevelev, Rishon-le-Zion (IL); Yacov Levron, Yehud Monoson (IL)

( * ) Notice: Subject to any disclaimer, the term of this patent is extended or adjusted under 35 U.S.C. 154(b) by 110 days.

(21) Appl. No.: 16/162,429

(22) Filed: Oct. 17, 2018

(65) Prior Publication Data

US 2019/0110738 A1    Apr. 18, 2019

Related U.S. Application Data

(60) Provisional application No. 62/573,710, filed on Oct. 18, 2017.

(51) Int. Cl.
*A61B 5/00* (2006.01)
*A61B 1/00* (2006.01)
(Continued)

(52) U.S. Cl.
CPC ........ *A61B 5/4337* (2013.01); *A61B 1/00096* (2013.01); *A61B 1/051* (2013.01);
(Continued)

(58) Field of Classification Search
CPC ............. A61B 5/4337; A61B 5/00096; A61B 5/14539; A61B 5/0507; A61B 1/303; A61B 6/563; A61B 8/488; A61B 8/483; A61B 5/0008; A61B 5/0035; A61B 5/01; A61B 5/05; A61B 5/1473; A61B 1/00096; A61B 1/051; A61B 8/12; A61B 8/4416; A61B 8/4461; A61B 8/4494; A61B 8/565;
(Continued)

(56) References Cited

U.S. PATENT DOCUMENTS

| 4,770,186 A | 9/1988 | Regas et al. |
| 6,530,888 B2 | 3/2003 | Smith et al. |

(Continued)

*Primary Examiner* — Carl H Layno
*Assistant Examiner* — Anh-Khoa N Dinh
(74) *Attorney, Agent, or Firm* — Haim M. Factor (57) ABSTRACT

A multifunctional measuring device for automatic examination of female genital organs, the measuring device having proximal and distal directions, and comprising: a device handle, located in the proximal direction, connected to an elongated, cylindrically-shaped intravaginal module having a longitudinal axis of symmetry, the intravaginal module located in the distal direction; a control and communications subsystem configured within the handle; and an optic module, an ultrasound module, a microwave module, and a thermal sensor array, configured within the intravaginal module and a chemical sensor array configured outside of the intravaginal module; and the control and communications subsystem connected with the optic, ultrasound, and microwave modules and with the thermal sensor array; the intravaginal module positioned intravaginally to scan female genital organs and at least two chosen from list including: the optic module; the ultrasound module; the microwave module; the thermal sensor array; and the chemical sensor array to perform intravaginal measurements.

13 Claims, 6 Drawing Sheets

(51) Int. Cl.
*A61B 5/145* (2006.01)
*A61B 5/05* (2006.01)
*A61B 1/303* (2006.01)
*A61B 8/08* (2006.01)
*A61B 5/01* (2006.01)
*A61B 1/05* (2006.01)
*A61B 8/00* (2006.01)
*A61B 5/1473* (2006.01)
*A61B 8/12* (2006.01)

(52) U.S. Cl.
CPC ............ *A61B 1/303* (2013.01); *A61B 5/0035* (2013.01); *A61B 5/0086* (2013.01); *A61B 5/01* (2013.01); *A61B 5/05* (2013.01); *A61B 5/0507* (2013.01); *A61B 5/1473* (2013.01); *A61B 5/14539* (2013.01); *A61B 8/12* (2013.01); *A61B 8/4416* (2013.01); *A61B 8/4461* (2013.01); *A61B 8/4494* (2013.01); *A61B 8/483* (2013.01); *A61B 8/488* (2013.01); *A61B 8/565* (2013.01); *A61B 5/002* (2013.01); *A61B 5/0008* (2013.01); *A61B 2560/0425* (2013.01); *A61B 2562/028* (2013.01); *A61B 2562/0238* (2013.01); *A61B 2562/063* (2013.01)

(58) Field of Classification Search
CPC .... A61B 2560/0425; A61B 2562/0238; A61B 2562/028; A61B 2562/063; A61F 2/005; A61M 25/00; A61P 15/02; A61N 1/18; A61N 1/20; A61N 1/32; A61N 2001/18
USPC .......................................... 600/425, 435, 43
See application file for complete search history.

(56) References Cited

U.S. PATENT DOCUMENTS

| | | | |
|---|---|---|---|
| 6,741,895 B1 | 5/2004 | Gafni et al. | |
| 6,896,653 B1* | 5/2005 | Vail, III | A61B 1/303 600/109 |
| 7,314,453 B2 | 1/2008 | Kuo | |
| 7,503,899 B2 | 3/2009 | Caillouette | |
| 8,715,204 B2 | 5/2014 | Webster et al. | |
| 9,579,081 B2 | 2/2017 | Boutet et al. | |
| 2003/0083590 A1* | 5/2003 | Hochman | A61B 5/04 600/549 |
| 2007/0213590 A1* | 9/2007 | Squicciarini | A61B 1/00101 600/172 |
| 2011/0190689 A1* | 8/2011 | Bennett | A61B 5/6846 604/21 |
| 2012/0184827 A1 | 7/2012 | Shwartz et al. | |
| 2015/0151122 A1 | 6/2015 | Pelger et al. | |
| 2017/0065249 A1 | 3/2017 | Ergorov | |

* cited by examiner

Detail A
FIG 3

Detail B
FIG 4

MULTIFUNCTIONAL MEASURING DEVICE FOR AUTOMATIC EXAMINATION OF FEMALE GENITAL ORGANS

FIELD OF THE INVENTION AND BACKGROUND

The current invention relates to female health and diagnostic tools and specifically to a multifunctional measuring device for automatic examination of female genital organs.

Traditionally, large-scale medical continues to be dictated by direct personal care of patients by a doctor in a medical facility. Although modern medical service providers have been largely successful using this model, a significant portion of the female population has nonetheless not been effectively addressed. The problem is especially apparent for women who have need for a periodic genital examination, but cannot do so for many reasons, such as, but not limited to: no medical facility located nearby; reluctance to visit a gynecologist; and lack of knowledge.

Because a significant portion of the female population has not been addressed, due to the reasons noted hereinabove, there has been a clear increase in specific female diseases. This situation exists in developed countries and is even more prevalent in third-world countries, where the results are catastrophic.

There is therefore a clear need to make periodic female genital examination more accessible to a wider cross-section of the female population worldwide.

Traditionally, various intravaginal examinations and diagnoses are typically performed in a clinical/hospital setting. Conditions such, as but not limited to: cervical cancer; infections; inflammation; and ovulation are diagnosed following examination performed by a trained technician and/or an experienced doctor using dedicated equipment. In almost all cases, the equipment employs one type of technology (at most two) to detect a targeted condition for diagnosis. Among the prior art are:

In U.S. Pat. No. 9,579,081, whose disclosure is incorporated by reference, Boutet et al. describe a device for a bimodal diagnostic probe with optical and ultrasonic imaging, the probe including a main body supporting an ultrasonic transducer at its front end. The device includes a shell, an illumination mechanism mounted on a front end of the shell to light outside of the shell, and a collection or detection mechanism mounted on the front end of the shell to collect or detect an optical signal produced outside the shell. The shell includes an attachment mechanism to reversibly assemble it around the main body of the probe, with the illumination mechanism and the collection or detection mechanism mounted on the shell.

Kuo, in U.S. Pat. No. 7,314,453, whose disclosure is incorporated by reference, describes a handheld diagnostic device having a test head and a handle is equipped with an open test channel having sensors and liquid reagent dispensing opening for the diagnostic testing of body fluids. The test channel can draw in fluid sample by capillary force and be closed by a channel cover for mixing the fluid sample with liquid reagent for electrochemical reactions for providing measurement signals for diagnostic analysis by a microprocessor included in the handle. A vibration means is added for stimulating the production of the body fluid sample and for assisting mixing of the sample solution. A renewable biosensor having a reusable electrode system and a dispensing means for providing a new dose of liquid reagent is included in the test head for repeated uses of the test channel and the biosensor. A dual-dispensers system having two reagent cartridges and two dispensing lines is included for simultaneous or selective dispensing of reagents for multiple diagnostic testing. The handheld device can be used for the self-diagnostic testing of saliva, body fluid, blood and vagina fluid for home healthcare and for monitoring predetermined components in a pourable fluid. For vagina fluid applications, a handheld diagnostic device may include cream or foam dispenser for dispensing vagina medication material, lubricant, or spermicide.

In U.S. Pat. No. 6,530,888, whose disclosure is incorporated herein by reference, Smith et al. describe a real-time three-dimensional ultrasound imaging probe apparatus is configured to be placed inside a body. The apparatus comprises an elongated body having proximal and distal ends with an ultrasonic transducer phased array connected to and positioned on the distal end of the elongated body. The ultrasonic transducer phased array is positioned to emit and receive ultrasonic energy for volumetric forward scanning from the distal end of the elongated body. The ultrasonic transducer phased array includes a plurality of sites occupied by ultrasonic transducer elements. At least one ultrasonic transducer element is absent from at least one of the sites, thereby defining an interstitial site. A tool is positioned at the interstitial site. In particular, the tool can be a fiber optic lead, a suction tool, a guide wire, an electrophysiological electrode, or an ablation electrode.

Regas et al., in U.S. Pat. No. 4,770,186, whose disclosure is incorporated herein by reference, describes a method and apparatus for predicting ovulation in a human female subject. The onset of menstruation of the subject is noted. Daily determinations are made of the electrical resistivity of the subject's saliva, beginning not more than five days following beginning of menstruation. The onset of ovulation is determined as a function of a peak resistivity measurement following onset of menstruation, which peak is followed by a nadir and subsequent sharp increase in saliva electrical resistivity measurement. Vaginal resistivity measurements may be made to confirm ovulation. A probe is used for the resistivity measurement. A probe includes a head or body with exposed imbedded electrodes.

In U.S. Pat. No. 6,741,895, whose disclosure is incorporated herein by reference, Gafni et al. describe a vaginal probe and method of use is disclosed for stimulation of the nerves of the vagina with the purpose of testing their reaction to stimuli in the hope of defining and treating sexual dysfunction in women. One embodiment of the invention includes a shaft adapted to be inserted into the genetalia of a human female. The shaft includes a stop, presented as a thickening of the shaft. The probe includes at least one stimulation area defined on a portion of the shaft so that only a selected portion of the genetalia [sic] is stimulated. The shaft may have sensors for measuring the reaction of the nerves to stimulation, and the stimulation areas may stimulate the nerves of the vagina using temperature, vibration, electricity, and/or pressure.

Shwartz et al., in US Patent Application Publication no. 20120184827, whose disclosure is incorporated herein by reference, describes a miniature medical spectrometer comprising: a room temperature, electrically excited, solid state two photon laser generating high intensity broad wavelength; a light projection optics, projecting said generated light on biological subject; a light collection optics, collecting reflected light from said biological subject; a wavelength selector spectrally analyzing said collected light; a detector, detecting said analyzed light; and a controller analyzing the reflected spectra and calculating result indicative of the medical state of the biological subject based on said spectrum.

In US Patent Application Publication no. 20170065249, whose disclosure is incorporated herein by reference, Ergorov describes a vaginal probe equipped with tactile sensors and ultrasound elements and configured for simultaneous acquisition of tactile images and ultrasound images for the same portion of vaginal tissues and pelvic floor muscles. The probe is configured for placement into vagina to record tactile images and ultrasound images in static, during tissue deformation as well as pelvic floor muscle contraction. Acquired and recorded tactile data are transmitted to a data processor for composing elasticity images of pelvic floor structures and muscle functional images and visually presenting thereof on a display.

Webster et al., in U.S. Pat. No. 8,715,204, whose disclosure is incorporated herein by reference, describe a temperature sensing device that can comprise an elastic ring structure. The temperature sensing device can further comprise a transducer device, such as a temperature sensor, and a microprocessor, memory and wireless transmitter. Such an arrangement can incorporate a passive (battery free), battery assisted or active battery powered transponder circuit with temperature measurement capability. The elastic ring structure can be forced in a spring-loaded state when elastically deformed thus becoming retained when disposed in a vaginal vault. In one embodiment, an active RF receiver or an RFID reader is brought in proximity to the temperature sensing and transmitting device arrangement, such as near a woman's pelvis from the outside to read the temperature and record it in a Central Processing Unit, CPU, associated with the receiver or RFID reader, such as a portable, handheld computer or wireless device.

In U.S. Pat. No. 7,503,899, whose disclosure is incorporated herein by reference, Caillouette describes an apparatus for quick screening for vaginal moisture pH level as related to a pre-selected pH level, comprising a manipulable [sic] element including a probe insertible into the vagina, at least one pH indicator on the element, the indicator characterized as producing a color which corresponds to pH level of vaginal moisture contacting the indicator, and a local comparison zone on the element having a color corresponding to a predetermined pH level, and positioned and shaped for quick color comparison with the color of the indicator after indicator contact with vaginal moisture. A test site for vaginosis may also be located on the probe, in non-interfering relation with said indicator and/or said zone.

Pelger et al., in US Patent Application publication no 20150151122, whose disclosure is incorporated herein by reference, describe a probe system for electro-stimulation and bio-feedback training of muscles in the pelvic floor region, in particular for pelvic floor physiotherapy and diagnosis, includes a probe having a probe body which is insertable into a vagina or a rectum, and a plurality of electrodes which are positioned at several locations along the length and around the circumference on the outer surface of the probe, the probe system further includes a control unit, operationally coupled to the probe, adapted for receiving EMG signals from each of the electrodes and for processing each of the signals for mapping the response of the muscles in the pelvic floor region.

Many of the prior art noted hereinabove include one or two technologies for intravaginal examination—performed by a doctor—for a defined, singular diagnosis/condition. None of the prior art use more than two combined technologies in one examination device. Furthermore, the prior art devices are directed only for clinical/hospital use by a trained individual and not for remote and/or home use.

There is therefore a need for an intravaginal examination device taking advantage of more than two combined technologies, the device being cheap, reliable, and simple to operate to identify and diagnose a spectrum of conditions. Furthermore, there is a need for an automatic device for intravaginal multifunctional examinations, remotely located from the clinic or hospital, and allowing transmission of examination data for detailed medical considerations, conclusions, and recommendations.

SUMMARY OF INVENTION

According to the teachings of the current invention, there is provided a multifunctional measuring device for automatic examination of female genital organs, the measuring device being sealed and having proximal and distal directions, the measuring device comprising: a device handle, located in the proximal direction, connected to an elongated, cylindrically-shaped intravaginal module having a longitudinal axis of symmetry, the intravaginal module located in the distal direction; a control and communications subsystem configured within the device handle; and an optic module, an ultrasound module, a microwave module, and a thermal sensor array, configured within the intravaginal module and a chemical sensor array configured outside of the intravaginal module; and the control and communications subsystem connected with the optic, ultrasound, and microwave modules and with the thermal sensor array; wherein the intravaginal module is positioned intravaginally to scan and examine female genital organs and at least two chosen from the list including: the optic module; the ultrasound module; the microwave module; the thermal sensor array; and the chemical sensor array, are used to perform intravaginal measurements. Preferably, the optic module includes at least one camera, the ultrasound module includes a plurality of ultrasound transceivers, the microwave module includes a plurality of microwave transceivers; and the thermal sensor array includes a plurality of thermal sensors. Most preferably, the at least one camera, the plurality of ultrasound and microwave transceivers, and the plurality of thermal sensors are positioned within a rotating tube, the rotating tube positioned and rotatable about the longitudinal axis of symmetry within a stationary distal transparent housing.

Typically, the chemical sensor array is configured outside of the stationary distal transparent housing and positioned within the field-of-view of the at least one camera, the chemical sensor array having pH indicative materials which change color. Most typically, an internal tube motive assembly includes a motor oriented parallel to the axis of symmetry, the motor configured to rotate the rotating tube and wherein the plurality of ultrasound transceivers and the plurality of microwave transceivers are positioned and pointed distally within the rotating tube. Preferably, an elongated tubular motive assembly housing is mechanically fixed coaxially and within the rotating tube and the at least one camera is attached distally to the motive assembly housing, the at least one camera oriented substantially coaxially with the axis of symmetry and pointing in the distal direction. Most preferably, the rotating tube includes a flat mirror interacting with the at least one camera, the flat mirror configured to assume a first position serving to reflect light substantially 90 degrees perpendicularly to the axis of symmetry and a second position serving to allowing light to pass unobstructed to the at least one camera. Typically, the rotating tube is simultaneously rotated about the axis of symmetry and the rotating tube is translated along the axis of symmetry.

Most typically, the at least one camera includes a plurality of cameras configured longitudinally along and within the rotating tube, wherein respective cameras point radially towards to the axis of symmetry. Preferably, the at least one camera further includes a distal camera positioned distally and coaxially within the rotating tube, the distal camera aimed distally and coaxially with the axis of symmetry. Most preferably, the plurality of thermal sensors configured longitudinally along and within the rotating tube. Typically, the control and communications subsystem includes a control module and a communications module and wherein data from intravaginal measurements are transferred to communications module. Most typically, the communications module transfers data from intravaginal measurements to remote centers for professional medical processing. Preferably, the drive motor is controlled by the control module to enable scanning and examination of female genital organs. Most preferably, the optic module is operated to provide images chosen from at least one in the list including: still images; video images; and infrared images.

LIST OF FIGURES

The invention is herein described, by way of example only, with reference to the accompanying drawings, wherein.

DETAILED DESCRIPTION

Embodiments of the current invention include a device intended for home use by women, and in examinations performed in medical facilities by qualified medical personnel. The device allows automatic measurement and visualization of several parameters of female genitalia, providing primary processing of examination data and subsequent transfer from remote locations to a medical facility for medical analysis, recommendations, and conclusions.

In the specification and claims which follow hereinbelow, the terms "ultrasound transceiver", "ultrasound transceiver/sensor", "ultrasonic Doppler", and "ultrasound doppler" are used interchangeably in the specification and claims hereinbelow and are intended to mean ultrasound tomography and ultrasound Doppler technologies, as known in the art.

Similarly, the expressions "microwave transceiver", "microwave transceiver/sensor", and "microwave Doppler" are used interchangeably in the specification and claims hereinbelow and are intended to mean microwave tomography and microwave Doppler technologies, as known in the art. As described more in detail hereinbelow, embodiments of the current invention, employing related and overlapping technologies in measurements and examinations of different medical features, enable improved correlation of measurement results, which has proven to be useful for medical conclusions.

Embodiments of the device of the current invention include a compact examination unit inserted into a woman's vagina, the unit which automatically measures, visualizes, and collects medical information regarding the physical condition of the woman's genitalia. Primary measured parameters, as described hereinbelow, are automatically processed and transferred to yield potential correlations regarding an array of medical conditions of the vagina and cervix. The device employs combined, complementary, technologies including: ultrasound Doppler; thermal; optic; and organic/chemical technologies and/or combined pairs of technologies to perform a number of intravaginal detections.

Embodiments of the current invention are directed to an intravaginal examination device taking advantage of more than two of the above-mentioned combined technologies, the apparatus being cheap, reliable, and simple to operate to affect identification and diagnosis of a spectrum of female conditions. The device can perform optical, ultrasonic, and electromagnetic scanning examinations using respective sensors, which are assembled into a singular housing. The device also includes a number of local measuring means, such as, but not limited to: an infra-red (IR) matrix sensor; pH sensor; and litmus. In this way, the device enables specialists located remotely in a medical facility to analyze the initial medical examination information for female health and to serve as a base for clinical examinations of the female population without the need for direct contact between a woman and doctors in a medical facility.

Figure 1:
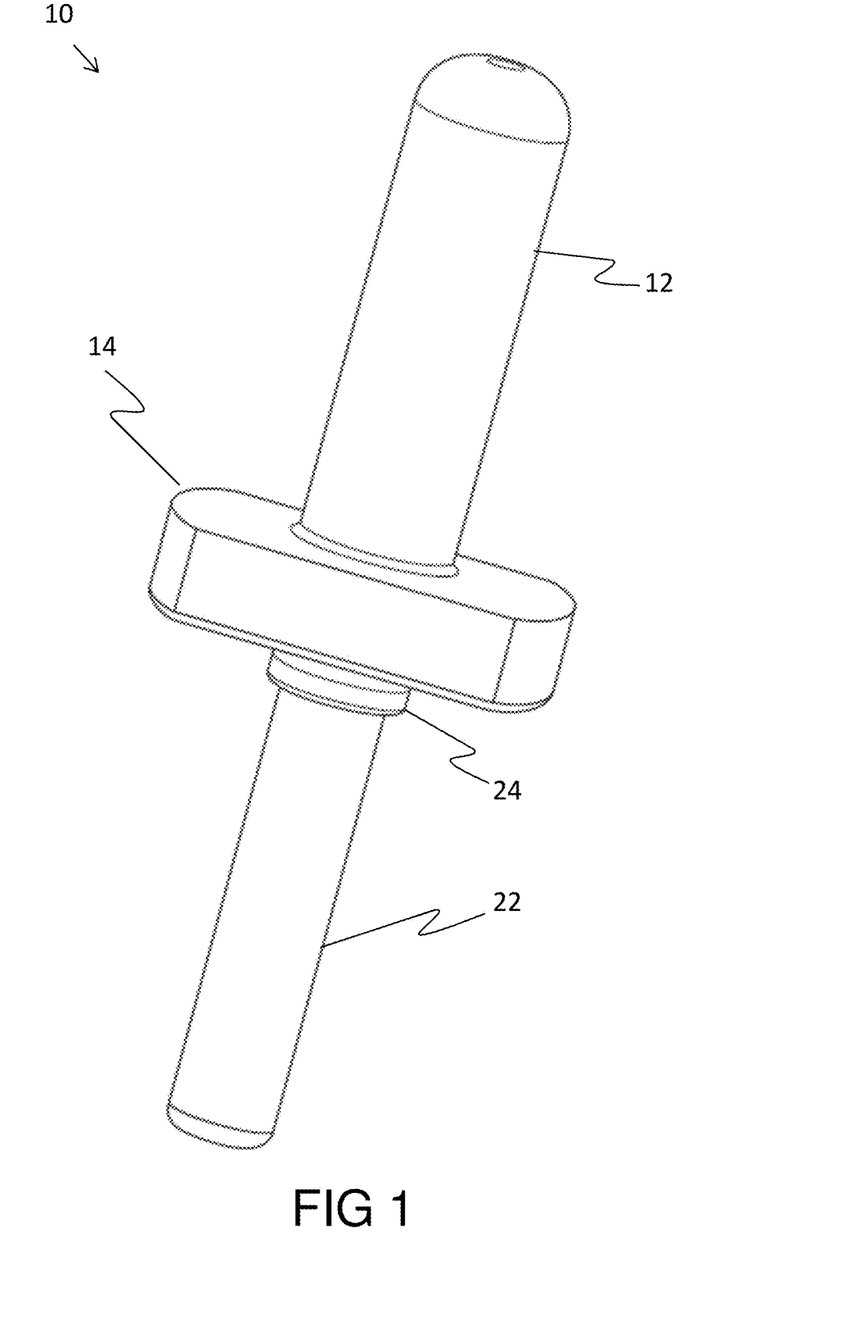
FIG. 1A is schematic pictorial view of a multifunctional measuring device for automatic examination of female genital organs, in accordance with embodiments of the current invention.

Reference is currently made to FIG. 1, which is a schematic pictorial view of a multifunctional measuring device for automatic examination of female genital organs 10, in accordance with embodiments of the current invention. Multifunctional measuring device 10 includes: a device handle 12; an attachment base 14; an intravaginal module 22 having an elongated cylindrical shape, having a diameter of approximately 2.5 cm; and an intravaginal module attachment, which connects the intravaginal module to the handle. Multifunctional measuring device 10 has proximal and distal directions, corresponding, respectively, to the direction towards the device handle and the direction towards the intravaginal module. The multifunctional measuring device is used by grasping the device handle and inserting the intravaginal module 22 into a vagina, for examination—as noted hereinabove and as further described hereinbelow. The multifunctional device, having electronic, mechanical, and optical components within, as described below, is sealed against moisture, as known in the art.

Figure 2:
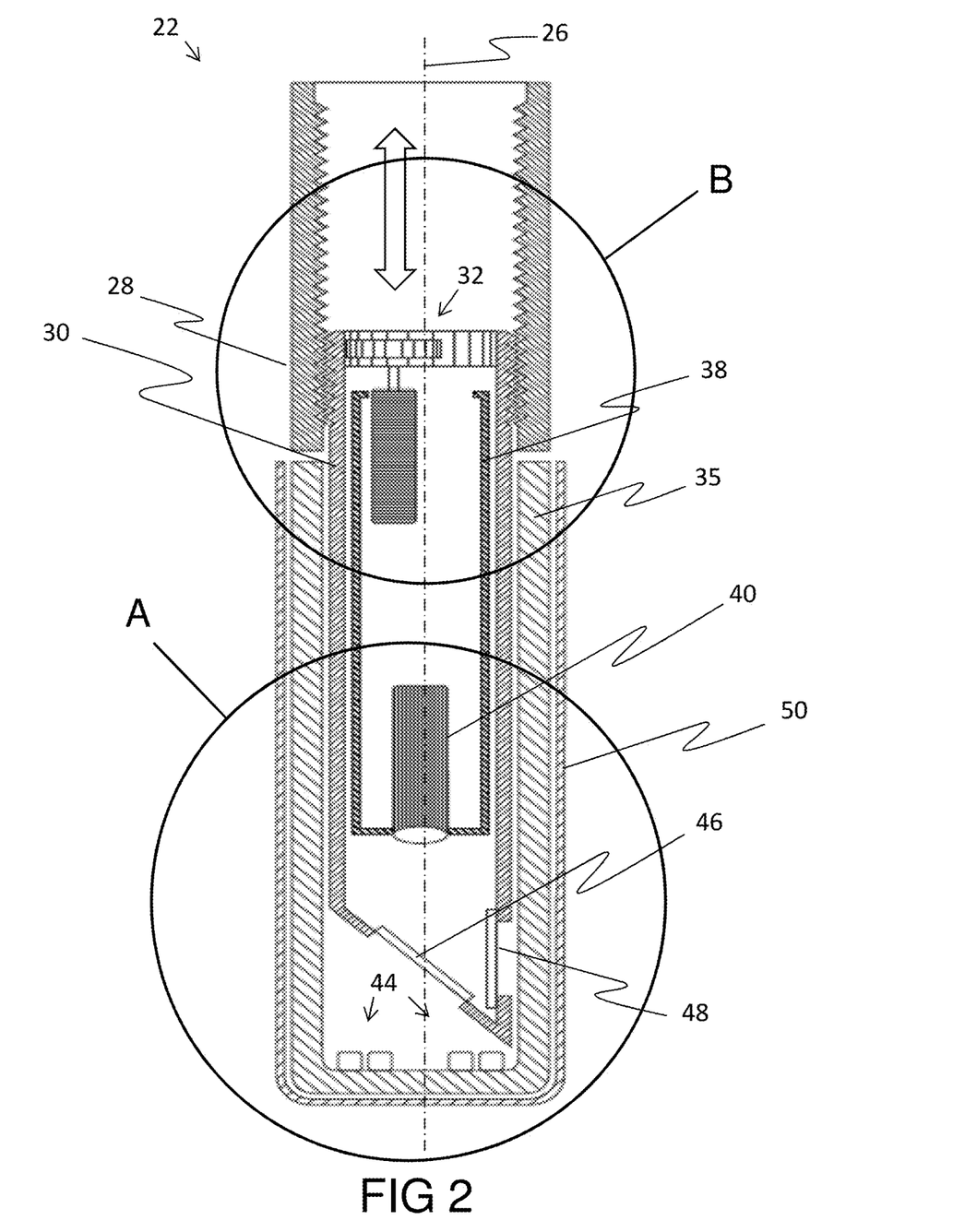
FIG. 2 is a cross-sectional view of the intravaginal module of FIG. 1, in accordance with an embodiment of the current invention.

Reference is currently made to FIG. 2, which is a cross-sectional view of intravaginal module 22 of FIG. 1, in accordance with an embodiment of the current invention. Intravaginal module 22 is identical in notation, configuration, and functionality to that shown in FIG. 1 and elements indicated by the same reference numerals and/or letters are generally identical in configuration, operation, and functionality as described hereinabove. Intravaginal module 22 is shown in the figure having a longitudinal axis of symmetry 26, indicating that the intravaginal module has a generally elongated-tubular structure, with additional elements being configured within the intravaginal module and with measurements/sensing being performed outside of the module (i.e. intravaginally), as described further hereinbelow. Intravaginal module 22 includes: a proximal enclosure tube 28; a rotating/translating internal tube 30; an internal tube motive assembly 32; a distal transparent housing 35, and a motive assembly housing 38—all having cylindrical shape and being coaxially configured with longitudinal axis of symmetry 26.

Rotating/translating internal tube 30 is configured concentrically to both proximal enclosure tube 28 and distal transparent housing 35 and the rotating/translating internal tube rotates and translates (as indicated by the arrow in the figure) as further described hereinbelow. A motive assembly housing 38 is configured concentrically within rotating/translating internal tube 30, with part of internal tube motive assembly 32 configured within motive assembly housing 38, as described further hereinbelow.

Additionally included in intravaginal module 22 are: a video camera 40; a transceiver array 44; a flat mirror in a first position 46; a flat mirror in a second position 48; and a disposable transparent cover 50, which serves to cover the intravaginal module, and which is replaced for each examination, as known in the art. The disposable transparent cover may additionally be used for chemical sensing, as described further hereinbelow. The camera is oriented substantially coaxially with the axis of symmetry and pointing in the distal direction (i.e. viewing light coming from the distal direction).

Figure 3:
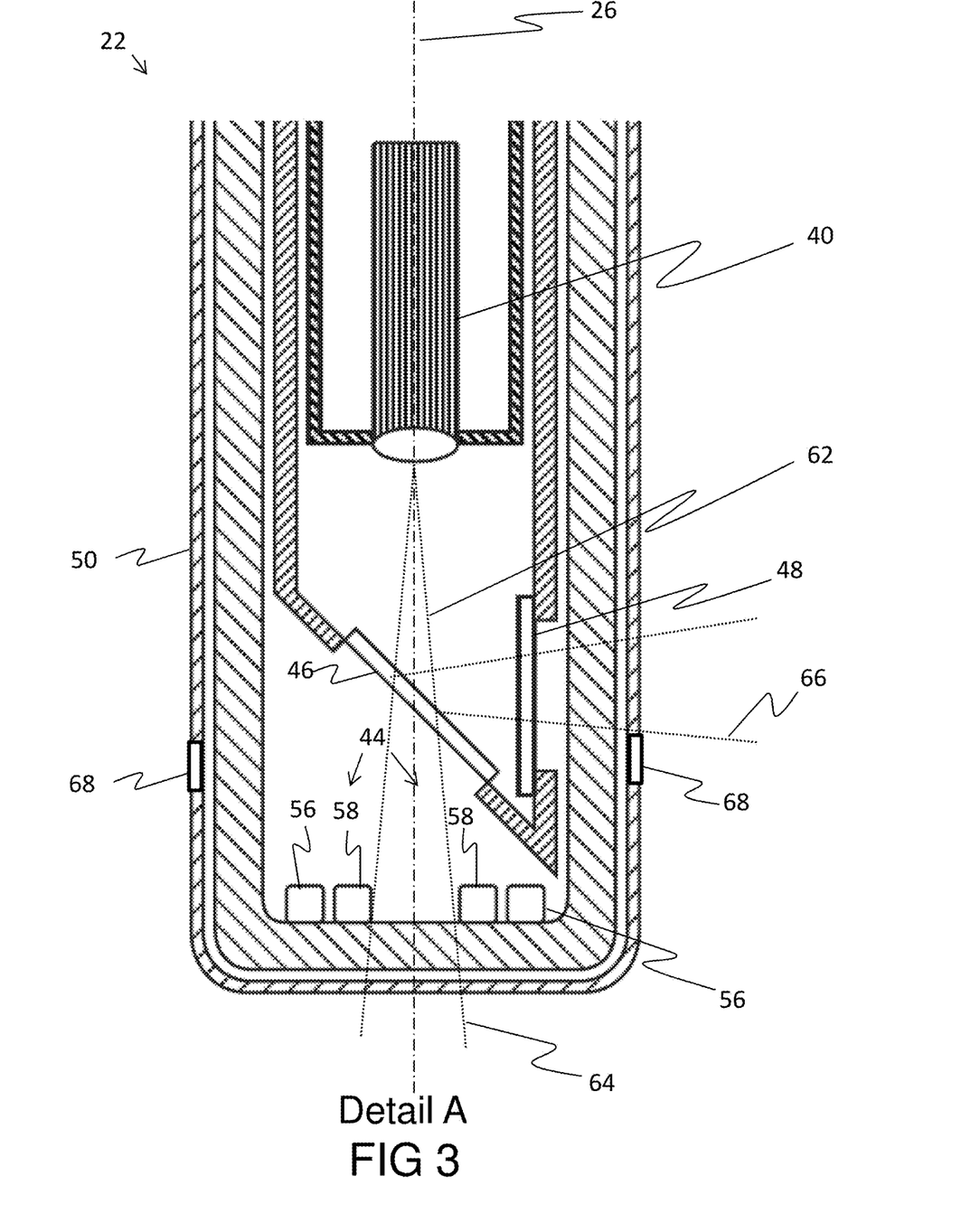
FIG. 3 is a detailed cross-sectional representation of the intravaginal module of FIG. 2, indicated as "Detail A", in accordance with an embodiment of the current invention.

Reference is currently made to FIG. 3, which is a detailed cross-sectional representation of intravaginal module 22 of FIG. 2, indicated as "Detail A", in accordance with an embodiment of the current invention. Intravaginal module 22 is identical in notation, configuration, and functionality to that shown in FIG. 2 and elements indicated by the same reference numerals and/or letters are generally identical in configuration, operation, and functionality as described hereinabove. Transceiver array 44 includes 2 pairs of an ultrasound transceiver/sensor 56 and a microwave transceiver/sensor 58. The sensors of transceiver array 44 serve to obtain an acoustic volumetric model (ultrasound doppler) and a microwave volumetric model (microwave Doppler) of the genitalia under examination.

The flat mirror is configured to allow camera 40 to view light passing substantially along longitudinal axis of symmetry 26, when the flat mirror is in second position 48 (allowing light to pass unobstructed to the camera)—as shown schematically by a video camera focal cone 62 and a continued video camera focal cone 64. When the flat mirror is in first position 48 (which is tilted substantially 45 degrees to the axis of symmetry, serving to reflect light substantially 90 degrees perpendicularly to the axis of symmetry) camera 40 views light passing substantially radially to the intravaginal module, as shown schematically by a reflected video camera focal cone 66. Typically, the flat mirror is hinged and controlled to precisely attain the first and the second positions—as known in the art (and not shown in the figure). The video camera additionally has an illumination source associated with it (not shown in the figure)—as known in the art.

The video camera, combined with translation and rotation of rotating/translating internal tube 30 by an internal tube motive assembly 32 (as described further hereinbelow) and positioning of the flat mirror (as described hereinabove), enable optical scanning in both radial and longitudinal directions to obtain a panoramic optical image of the examined vagina.

At least one disposable chemical sensor element 68 is configured exterior to the distal transparent housing of the intravaginal module. Configurations of the chemical sensor may include, but not be limited to: integration into a form such as an "O-ring" place around the exterior of the intravaginal module; integration into disposable transparent cover 50; and a combination of "O-ring" and disposable transparent cover configurations. The chemical sensor may include, but not be limited to litmus pH indicative materials which change color, as known in the art, when contacting bodily fluids—and more than one calibrated disposable chemical sensor element 68 may be used for an examination; thereby giving additional range and or precision in measuring pH, as known in the art. The at least one disposable chemical sensor element is positioned within the field-of-view of the camera; thereby enabling the camera to view and allow recording the chemical sensor element(s) color for further analysis, as described hereinbelow.

Figure 4:
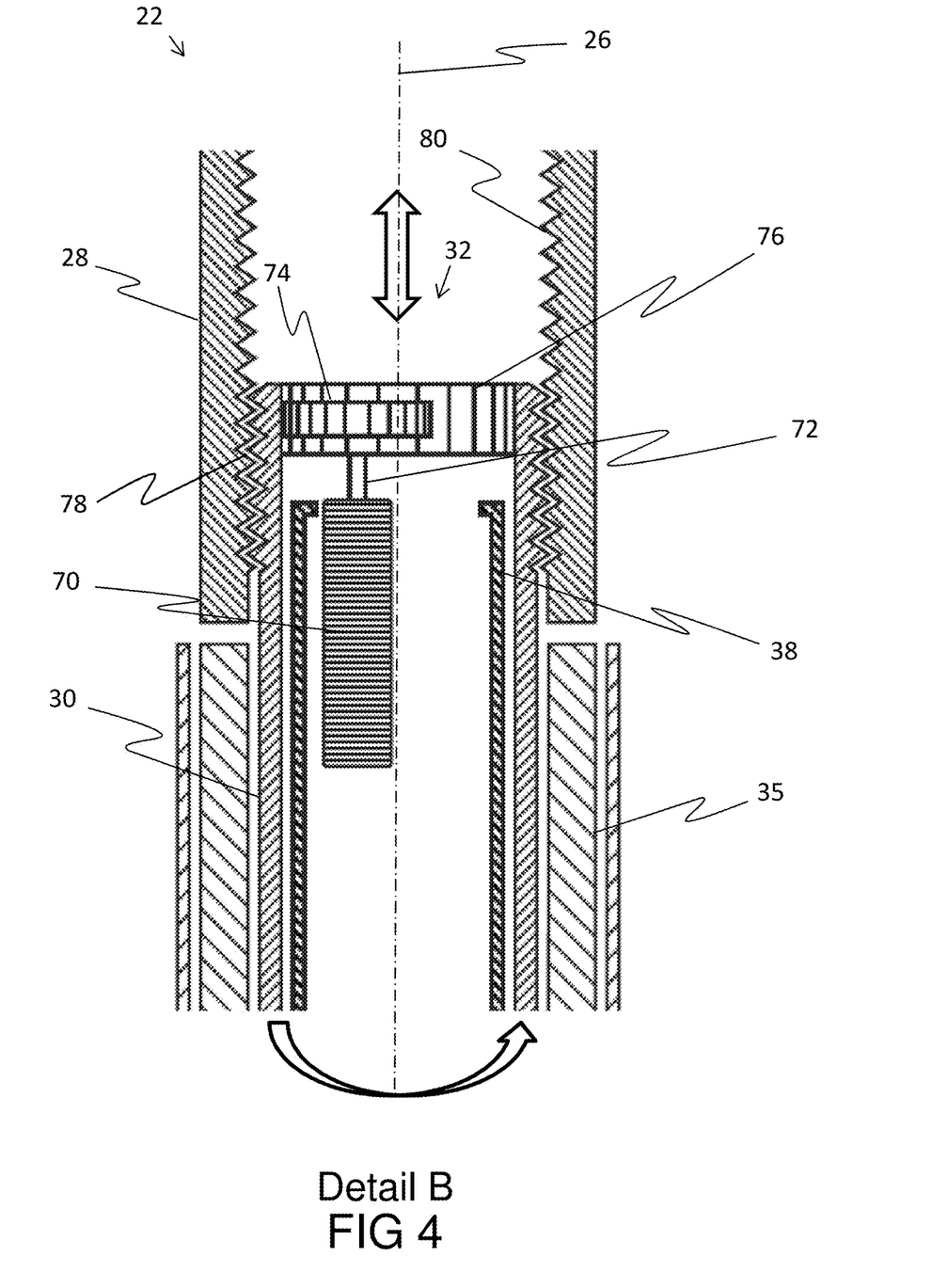
FIG. 4 is a detailed cross-sectional representation of the intravaginal module of FIG. 2, indicated as "Detail B", in accordance with an embodiment of the current invention.

Reference is currently made to FIG. 4, which is a detailed cross-sectional representation of intravaginal module 22 of FIG. 2, indicated as "Detail B", in accordance with an embodiment of the current invention. Intravaginal module 22 is identical in notation, configuration, and functionality to that shown in FIGS. 2 and 3, and elements indicated by the same reference numerals and/or letters are generally identical in configuration, operation, and functionality as described hereinabove. Internal tube motive assembly 32 includes: a drive motor 70; a drive motor axle 72; a threaded gear wheel 74, driven by the motor, as shown; and an internally-threaded drive tube 76 which is driven by threaded gear wheel 74. At the proximal end of Rotating/translating internal tube 30 has an external threading 78 configured proximally on the rotating/translating internal tube, the external threading corresponding to an internal threading 80 configured distally on the proximal enclosure tube 28. Internal tube motive assembly 32 further includes two limit two limit switches (not shown in the figure) that serve to interact with control of the internal motive assembly with respect to end positions of the assembly.

Motive assembly housing 38 is positioned and mechanically fixed coaxially and within rotating/translating internal tube 30. The rotating/translating internal tube is engaged within and rides substantially concentrically and coaxially within the proximal enclosure tube, due to engagement of external threading 78 and internal threading 80, as described hereinabove. Drive motor 70 is mechanically fixed to motive assembly housing 38. Internally-threaded drive tube 76 is mechanically fixed concentrically and within rotating/translating internal tube 30 at the proximal end of rotating/translating internal tube. Drive motor 70 may be either of DC or step motor type, mutandis mutatis.

Rotation and translation of rotating/translating internal tube 30 take place by operating drive motor 70, which drives threaded gear wheel 74. The threaded gear wheel drives internally-threaded drive tube 76, which is mechanically coupled to and which drives rotating/translating internal tube 30, imparting both rotational and translation movement of the rotating/translating internal tube with regard to distal transparent housing 35. The rotational and translation movement of internal tube 30 is indicated schematically in the figure by the two arrows: one in an axial direction and one in a radial direction. In this way, the camera and other sensing elements described hereinabove and further below are both rotated and translated within intravaginal module 22 to perform various sensing and measuring functions.

Figure 5:
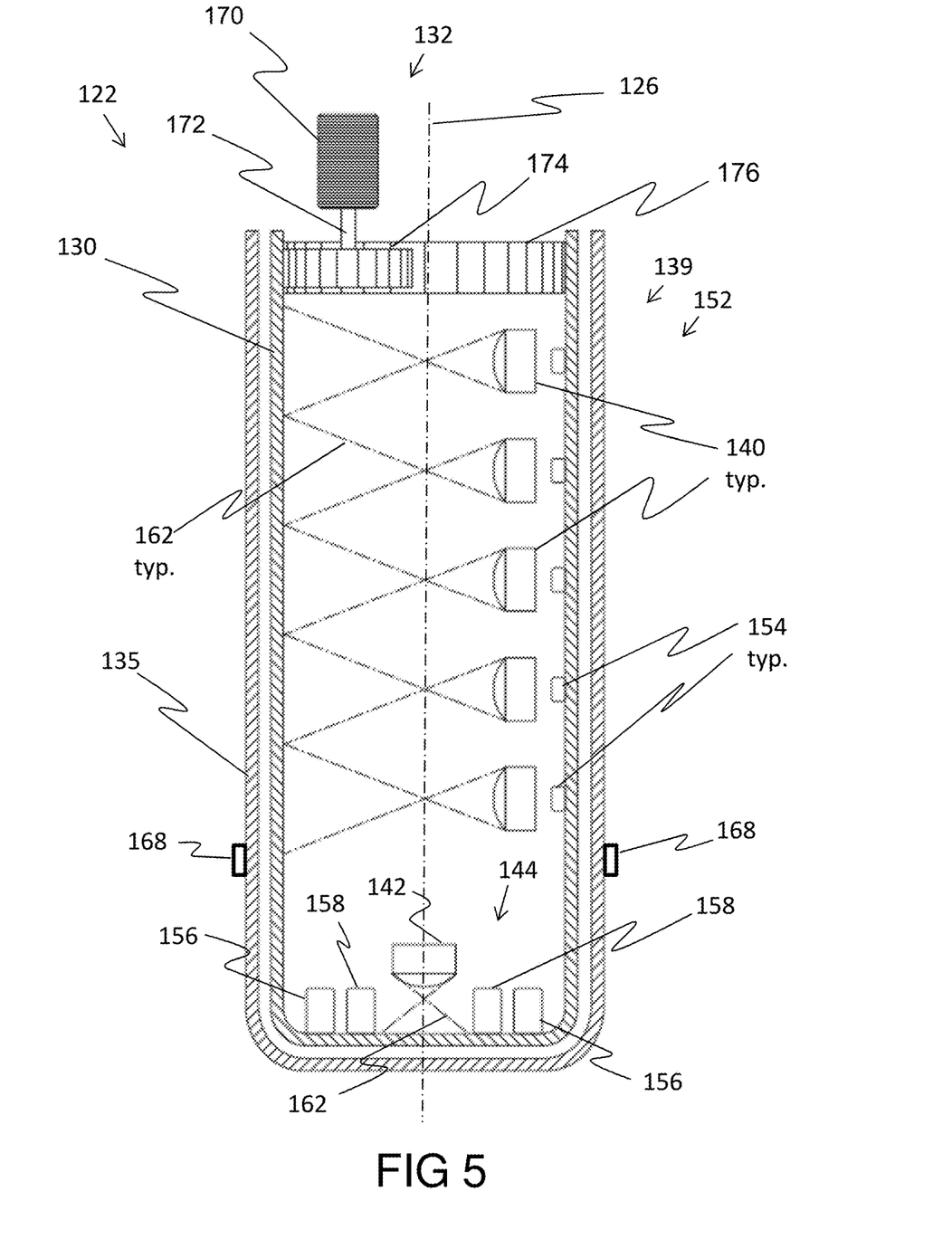
FIG. 5 is a cross-sectional view of an alternate-or-optional intravaginal module, similar to the intravaginal module of FIG. 1, in accordance with an embodiment of the current invention.

Reference is currently made to FIG. 5, which is a cross-sectional view of alternate-or-optional intravaginal module 122, similar to intravaginal module 22 of FIG. 1, in accordance with an embodiment of the current invention. Alternate-or-optional intravaginal module 122 is shown in the figure having a longitudinal axis of symmetry 126, indicating that the intravaginal module has a generally elongated-tubular structure (similar to intravaginal module 22 of FIG. 1), with additional elements being configured within the intravaginal module and measurements/sensing being performed outside of the module (i.e. intravaginally), as described previously and hereinbelow. Intravaginal module 122 includes: a rotating internal tube 130; and a distal transparent housing 135—both having cylindrical shape and being coaxially configured with longitudinal axis of symmetry 126.

Rotating internal tube 130 rotates within distal transparent housing 135 as further described hereinbelow. A motive assembly housing 132 is configured at a proximal end of the rotating internal tube, the motive assembly housing including: a drive motor 170; a drive motor axle 172; a threaded gear wheel 174, driven by the motor, as shown; and an internally-threaded drive tube 176 which is driven by threaded gear wheel 174. Drive motor 170 positioned and mechanically fixed at the proximal end of intravaginal module 122 (fixture of the drive motor not shown in the figure) with respective threading of threaded gear wheel 174 and internally-threaded drive tube 176 are engaged. As a result, the rotating internal tube is engaged within and rides substantially concentrically and coaxially within the proximal enclosure tube. Drive motor 170 may be either of DC or step motor type, mutandis mutatis.

Rotation of rotating internal tube 130 take place by operating motor 170, which drives threaded gear wheel 174. The threaded gear wheel drives internally-threaded drive tube 176, which is mechanically coupled to and which drives rotating internal tube 130, imparting rotational movement of the rotating internal tube with regard to distal transparent housing 135. The rotational movement of internal tube 130 enables sensing elements, described hereinbelow, to be rotated within alternate-or-optional intravaginal module 122 to perform various sensing and measuring functions, as discussed hereinbelow.

Alternate-or-optional intravaginal module 122 includes: a video camera array 139 (comprising a plurality of video camera assemblies 140); a distal video camera assembly 142; a transceiver array 144; and a thermal sensor array 152. Distal video camera 142 is positioned substantially coaxially and pointed in the distal direction pointed at the distal end distal transparent housing 135. Thermal sensor array 152 includes a plurality of thermal sensors 154. The plurality of thermal sensors is configured longitudinally within and in contact with rotating internal tube 130. The longitudinal configuration of plurality of thermal sensors 154 enables localized thermal measurement along the intravaginal module. The plurality of thermal sensors may include but is not limited to: infra-red and contact thermal sensors. The plurality of thermal sensors, combined with the rotational movement of the rotating internal tube, serves to obtain a circular panoramic temperature map, as known in the art, of the examined vagina.

Transceiver array 144 includes: at least one ultrasound transceiver 156 and at least one microwave transceiver 158. The at least one transceivers of transceiver array 144 serve to obtain an acoustic volumetric model (ultrasound doppler) and a microwave volumetric model (microwave Doppler) of the genitalia under examination.

The plurality of video camera assemblies is configured longitudinally within rotating internal tube 130, the respective individual camera pointing radially (i.e. perpendicularly to) and towards the longitudinal axis of symmetry. Respective video camera focal cones 162 are indicated schematically in the figure to indicate respective fields-of view of the video camera assemblies. As rotating internal tube 130 is rotated, as described hereinabove, the plurality of video camera assemblies view light passing substantially radially to the intravaginal module, as shown schematically by the respective video camera focal cones. In the case of distal video camera 142, which is positioned and aimed substantially coaxially with axis 126 as indicated in the figure, the distal camera maintains its distal-pointing as rotating internal tube 130 is rotated. Video camera assemblies 140 and distal video camera 142 additionally have an illumination source associated with them (not shown in the figure)—as known in the art. The plurality of video camera assemblies and the distal video camera 142 serve to obtain a panoramic optical image of the examined vagina.

A disposable transparent cover (not shown in the figure) is configured exteriorly to distal transparent housing 135, similar to disposable transparent cover 50 of alternate-or-optional intravaginal module 122 (ref FIGS. 2 and 3).

Similar to intravaginal module 22 shown in FIG. 3 hereinabove, alternate-or-optional intravaginal module 122 includes at least one disposable chemical sensor element 168 configured exterior to the alternate-or-optional intravaginal module. Configurations of the chemical sensor may include, but not be limited to: integration into a form such as an "O-ring" place around the exterior of the intravaginal module; integration into the disposable transparent cover; and a combination of "O-ring" and the disposable transparent cover configurations. The chemical sensor may include, but not be limited to litmus pH indicative materials which change color, as known in the art, when contacting bodily fluids—and more than one calibrated disposable chemical sensor element 168 may be used for an examination; thereby giving additional range and or precision in measuring pH, as known in the art. The at least one disposable chemical sensor element is positioned within the field-of-view of the camera assemblies; thereby enabling the camera assemblies to view and enable recording the chemical sensor element(s) color for further analysis.

Figure 6:
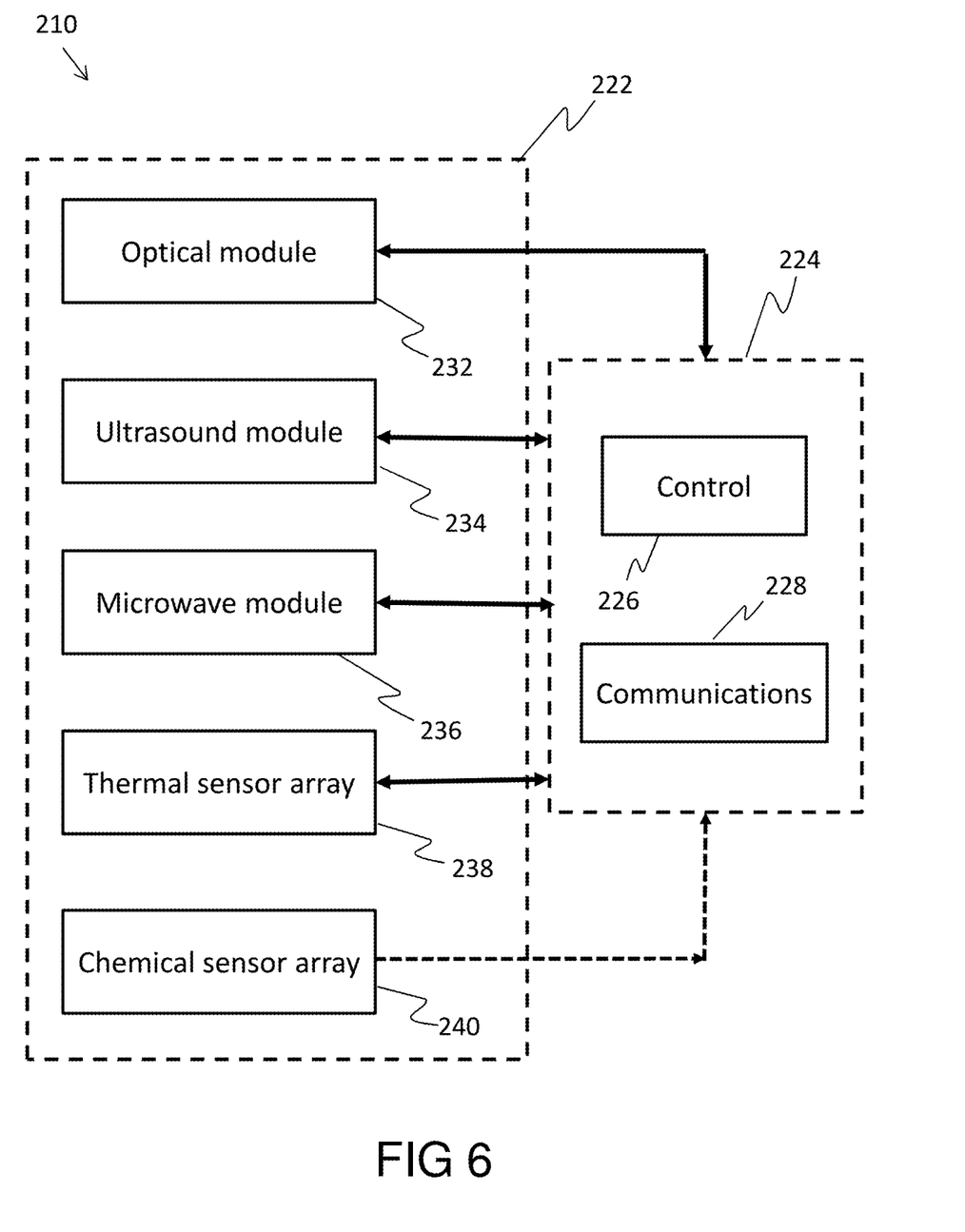
FIG. 6 is a schematic structure-functional block diagram of a multifunctional measuring device for automatic examination of female genital organs and an intravaginal module, in accordance with embodiments of the current invention.

Reference is currently made to FIG. 6, which is a schematic structure-functional block diagram of a multifunctional measuring device 210 for automatic examination of female genital organs and an intravaginal module 222, in accordance with embodiments of the current invention. Multifunctional measuring device 210 and intravaginal module 222 are identical in notation, configuration, and functionality to multifunctional measuring device 10 and to intravaginal module 22 shown in FIGS. 1-4 and intravaginal module 122 shown in FIG. 5.

Multifunctional measuring device 210 includes a control and communications subsystem 224, comprising a control module 226 and a communications module 228. Control module 226 includes hardware and functionality related, but not limited to: micro-processing, logic, data storage, and power storage and management; whereas communications module 228 includes hardware and functionality related, but not limited to wired and wireless communications/data transfer to local and remote locations. Power storage and management hardware and functionality included in the control module further includes power sources/connections, such as, but not limited to: battery power and mains power.

As described hereinabove with regard to FIGS. 2-5, intravaginal module 222 also includes: an optical module 232; an ultrasound module 234; a microwave module 236; a thermal sensor array 238; and a chemical sensor array 240. As indicated in the figure, the optical, ultrasound, and microwave modules and thermal array all send signals (sensor data, telemetry) to the control and communications subsystem, and the control and communications subsystem likewise sends command and control signals to the optical, ultrasound, and microwave modules and thermal array to perform measurements.

Specifically, the control module controls the drive motor and flat mirror positioning described hereinabove (FIGS. 2, 4, and 5) to obtain desired sensor and camera scanning of segments of the examined vagina. Video images of the vaginal segments are received by the camera, are images are converted to the desired digital form and transferred to control and communications subsystem 224.

Optical module 232 is operated to provide images including but not limited to: still images; video images; and infrared images in a wide range of resolutions and combinations (as above) to cross-correlate/verify and/or complement examinations and obtain more complete and exact intravaginal examination results.

Similarly, the control module controls rotation and scanning by Doppler and microwave sensors (of ultrasound module 234 and microwave module 236) to desired segments of the examined vagina. Acoustic and microwave doppler images of the vaginal segments are received by the respective ultrasound and microwave modules and the images are converted to the desired digital form and transmitted to the control and communications subsystem. Alternatively, or optionally, embodiments of the current invention include configuring respective ultrasound and microwave Doppler sensors to have fixed orthogonally-directed sensor patterns. In this way a limited number of respective acoustic and microwave images are used to generate 3D volumetric models of the examined vagina.

In similar fashion, control module 226 controls the thermal sensor array, with measured localized temperatures in the examined vagina being converted into a digital form and transferred onward.

As noted hereinabove chemical sensor array 240 is sensed/measured by controlling the optical module.

All measured data is transferred to communications module 228 for transmission to remote centers for professional medical processing and/or interpretation.

Hardware associated with control and communications subsystem 224 is configured within the handle (ref handle 12, FIG. 1), whereas hardware associated with the optical, ultrasound, and microwave modules and thermal and chemical sensor arrays is located in the intravaginal module and the alternate-or-optional intravaginal module, as described in detail in FIGS. 2-5 hereinabove.

Applications and Use of the Multifunctional Measuring Device

In an embodiment of the current invention, combined Doppler/thermal/chemical/biological technologies are employed to detect intravaginal viruses. Vaginal viruses change pH level and deleteriously affect vaginal walls. When the vaginal walls are affected (either by blisters or cuts) local blood circulation and temperature are increased relative to the surroundings.

Focused thermal sensors sense a local relative temperature increase. Focused Doppler sensors senses local blood circulation increase. Chemical/biological sensors (based on litmus) sense vaginal pH levels. A combined result from sensor data yields sufficient information to identify vaginal virus types.

In another embodiment of the current invention, Doppler and optic technologies are used together to detect cervical cancer. Every cell type has its self-resonance. Self-resonance is dependent on a number of factors such as: mass; size; and temperature of the cell. Cancerous cells are larger and heavier than normal cells and resultantly have different self-resonance.

Using focused Doppler technology, resonant frequencies are detected in the patient according to the formula:

$$Fd=Fo*(1-(C-Vd)/(C+Vd))$$

Fd—frequency proportional to self-resonance motion
Fo—tested frequency or carrier frequency
C—Speed of light/sound in specific spaces/materials
Vd—self-resonance motion The resonant frequency data, as above, is transferred to an analysis subsystem, which processes the frequencies obtained (using FFT or any other appropriate transform/technique) to determine if frequencies characteristic of cervical cancer (typically ranging from 100 to 130 Hz) are among the frequencies obtained. A measurement of thermal change in the cervix using a thermal sensor verifies/cross references the Doppler results. Results are outputted by the processor following processing.

In yet another embodiment of the current invention, biologic/chemical/Doppler technologies are combined to detect an intravaginal inflammatory-fungal response. Changes in vaginal secretion may be detected by density changes of the material and reaction of appropriate litmus materials. Density or resistivity may be detected by waves reflected to a Doppler sensor. Wave intensity and/or the change in wave intensity and their angle of reflection allow calculation of the patient's material resistivity. Resistivity is proportional to density or change in density (when rapid changes in density are present).

Biological/chemical sensors serve to examine the secretion. Appropriate litmus materials positioned on the condom change their state according to the composition of the secretion and acidity of the environment (during contact). Optical sensors detect litmus changes.

Both optical and chemical technologies complement and verify/cross-reference the full and exact results.

And in another embodiment of the current invention, a combination of chemical, Doppler, and thermal technologies are applied to detect ovulation.

Cervical secretion changes during ovulation. (When there is no ovulation, secretion is viscous, whereas during ovulation secretion is less viscous.) Vaginal temperature changes during ovulation.

As noted hereinabove, changes in secretion may be detected by density changes of the material and reaction of appropriate litmus materials. Density or resistivity may be detected by waves reflected to a Doppler sensor. Wave intensity and/or the change in wave intensity and their angle of reflection allow calculation of the patient's material resistivity. Resistivity is proportional to density or change in density (when rapid changes in density are present).

The control and communications subsystem serves to processes data and provide diagnostic information according to ovulation status.

It will be appreciated that the above descriptions are intended only to serve as examples, and that many other embodiments are possible within the scope of the present invention as defined in the appended claims.

The invention claimed is:

1. A multifunctional measuring device for automatic examination of female genital organs, the measuring device being sealed and having proximal and distal directions, the measuring device comprising:

a device handle, located in the proximal direction, connected to an elongated, cylindrically-shaped intravaginal module having a longitudinal axis of symmetry, the intravaginal module located in the distal direction;

a control and communications subsystem configured within the device handle; and an optic module including at least one camera, an ultrasound module including a plurality of ultrasound transceivers, a microwave module including a plurality of microwave transceivers, and a thermal sensor array including a plurality of thermal sensors, configured within the intravaginal module and a chemical sensor array configured outside of the intravaginal module; and the control and communications subsystem connected with the optic, ultrasound, and microwave modules and with the thermal sensor array;

wherein the intravaginal module is positioned intravaginally to scan and examine female genital organs and at least two chosen from the list including: the optic module; the ultrasound module; the microwave module; the thermal sensor array; and the chemical sensor array, are used to perform intravaginal measurements; and wherein the at least one camera, the plurality of ultrasound and microwave transceivers, and the plurality of thermal sensors are positioned within a rotating tube, the rotating tube positioned and rotatable about the longitudinal axis of symmetry within a stationary distal transparent housing.

2. The measuring device of claim 1, wherein the optic module is operated to provide images chosen from at least one in the list including: still images; video images; and infrared images.

3. The measuring device of claim 1, wherein the chemical sensor array is configured outside of the stationary distal transparent housing and positioned within the field-of-view of the at least one camera, the chemical sensor array having pH indicative materials which change color.

4. The measuring device of claim 3, wherein an internal tube motive assembly includes a motor oriented parallel to the axis of symmetry, the motor configured to rotate the rotating tube and wherein the plurality of ultrasound transceivers and the plurality of microwave transceivers are positioned and pointed distally within the rotating tube.

5. The measuring device of claim 4, wherein an elongated tubular motive assembly housing is mechanically fixed coaxially and within the rotating tube and the at least one camera is attached distally to the motive assembly housing, the at least one camera oriented substantially coaxially with the axis of symmetry and pointing in the distal direction.

6. The measuring device of claim 5, wherein the rotating tube includes a flat mirror interacting with the at least one camera, the flat mirror configured to assume a first position serving to reflect light substantially 90 degrees perpendicularly to the axis of symmetry and a second position serving to allowing light to pass unobstructed to the at least one camera.

7. The measuring device of claim 6, wherein the rotating tube is simultaneously rotated about the axis of symmetry and the rotating tube is translated along the axis of symmetry.

8. The measuring device of claim 4, wherein the at least one camera includes a plurality of cameras configured longitudinally along and within the rotating tube, wherein respective cameras point radially towards to the axis of symmetry.

9. The measuring device of claim 8, wherein the at least one camera further includes a distal camera positioned distally and coaxially within the rotating tube, the distal camera aimed distally and coaxially with the axis of symmetry.

10. The measuring device of claim 9, wherein the plurality of thermal sensors configured longitudinally along and within the rotating tube.

11. The measuring device of claim 4, wherein the control and communications subsystem includes a control module and a communications module and wherein data from intravaginal measurements are transferred to communications module.

12. The measuring device of claim 11, wherein the communications module transfers data from intravaginal measurements to remote centers for professional medical processing.

13. The measuring device of claim 11, wherein the motor is controlled by the control module to enable scanning and examination of female genital organs.

* * * * *